(12) United States Patent
Rogers et al.

(10) Patent No.: US 9,161,598 B2
(45) Date of Patent: Oct. 20, 2015

(54) OPHTHALMIC DEVICES FOR DELIVERY OF BENEFICIAL AGENTS

(71) Applicant: CooperVision International Holding Company, LP, St. Michael (BB)

(72) Inventors: Victoria Rogers, Pleasanton, CA (US);
Andrew Luk, Pleasanton, CA (US);
Arthur Back, Danville, CA (US);
Samuel Zalipsky, Redwood City, CA (US)

(73) Assignee: CooperVision International Holding Company, LP, St. Michael (BB)

( * ) Notice: Subject to any disclaimer, the term of this patent is extended or adjusted under 35 U.S.C. 154(b) by 87 days.

(21) Appl. No.: 14/109,977

(22) Filed: Dec. 18, 2013

(65) Prior Publication Data

US 2014/0174957 A1 Jun. 26, 2014

Related U.S. Application Data

(60) Provisional application No. 61/740,617, filed on Dec. 21, 2012.

(51) Int. Cl.
*C08L 43/02* (2006.01)
*C08L 83/04* (2006.01)
*G02C 7/04* (2006.01)
*G02B 1/04* (2006.01)
*A45C 11/00* (2006.01)

(52) U.S. Cl.
CPC ............ *A45C 11/005* (2013.01); *C08L 43/02* (2013.01); *C08L 83/04* (2013.01); *G02B 1/043* (2013.01); *G02C 7/049* (2013.01)

(58) Field of Classification Search
CPC ........... C08L 43/02; C08L 83/04; G02C 7/04; G02B 1/043
See application file for complete search history.

(56) References Cited

U.S. PATENT DOCUMENTS

2003/0186825 A1 10/2003 Mitani et al.
2011/0305898 A1 12/2011 Zhang et al.

FOREIGN PATENT DOCUMENTS

| EP | 1245636 A1 | 10/2002 |
| EP | 1870736 A1 | 12/2007 |
| WO | 2008144247 A1 | 11/2008 |

OTHER PUBLICATIONS

International Search Report and Written Opinion issued in corresponding International Patent Application No. PCT/GB2013/053390 dated Jul. 24, 2014 (13 pages).
International Preliminary Report on Patentability issued in corresponding International Patent Application No. PCT/GB2013/053390 dated Dec. 23, 2014 (11 pages).
Communication Relating to the Results of the Partial International Search issued in corresponding International Patent Application No. PCT/GB2013/053390 dated Mar. 20, 2014 (4 pages).

*Primary Examiner* — Caixia Lu
(74) *Attorney, Agent, or Firm* — Kilyk & Bowersox, P.L.L.C.

(57) ABSTRACT

Contact lenses comprising phosphorylcholine groups release beneficial polyionic or guanidinium-containing agents.

14 Claims, No Drawings

OPHTHALMIC DEVICES FOR DELIVERY OF BENEFICIAL AGENTS

This application claims the benefit under 35 U.S.C. §119 (e) of prior U.S. Provisional Patent Application No. 61/740,617, filed Dec. 21, 2012, which is incorporated in its entirety by reference herein.

BACKGROUND

The field of the disclosure is ophthalmic devices for administering beneficial agents.

Contact lenses for administering ophthalmic drugs and other beneficial agents to the ocular tissue of a patient have been described. For example, the anionic contact lens material, etafilcon A, has been used in clinical studies to deliver or administer ketotifen, an anti-allergy drug used in the treatment of allergic conjunctivitis (see ClinicalTrials.gov NCT00569777). A problem associated with some ocular delivery devices is that they can be limited in the type of beneficial agent that the device is capable of administering. Another problem associated with some ocular drug delivery devices is that they involve complex manufacturing methods which are not amenable to large-scale manufacturing operations. We have discovered improved methods of manufacturing beneficial agent-releasing contact lenses that address these problems.

Contact lens packages including a sealed receptacle that contains a contact lens made of a silicone hydrogel copolymer in a sterile solution which comprises a stabilizing agent which can form an ionic complex or hydrogen bond with the hydrogel copolymer, have been described in U.S. Pat. Publ. No. 2007/0149428. A packaging system and method for the storage of an ionic hydrogel lens that uses an aqueous packing solution which includes a phosphorylcholine polymer, and which further can include a buffering agent, have been described in U.S. Pat. Publ. No. 2009/0100801. Other background publications include U.S. Pat. Publ. No. 2008/0085922, U.S. Pat. Publ. No. 2007/0265247, U.S. Pat. Publ. No. 2007/20100239637, U.S. Pat. Publ. No. 2008/0124376, U.S. Pat. No. 7,841,716, Karlgard et al, Int J Pharm (2003) 257:141-51 and Soluri et al., Optom Vis Sci (2012) 89:1140-1149.

SUMMARY

In one aspect, the invention provides a contact lens that comprises a hydrogel comprising integral phosphorylcholine groups and an ionic agent. Advantageously the ionic agent is electrostatically bound to the phosphorylcholine groups and releases from the lens upon wear by a patient. The ionic agent is polyionic or comprises at least one guanidinium group or is both polyionic and comprises at least one guanidinium group.

In a further aspect, the invention provides a method of manufacturing a contact lens. The method comprises polymerizing a monomer mixture comprising 2-methacryloyloxyethyl phosphorylcholine (MPC) to provide a non-hydrated lens-shaped polymerization product, immersing the non-hydrated lens-shaped polymerization product in a package containing a packaging solution comprising an ionic agent, and sealing the package. Exemplary monomer mixtures comprise 10 wt. % to 20 wt. % MPC. Exemplary ionic agents are polyionic and/or comprises at least one guanidinium group. The method may further comprise autoclaving the sealed package.

DETAILED DESCRIPTION

We have discovered unique properties of phosphorylcholine (PC)-containing hydrogel contact lenses which can be utilized to deliver beneficial ionic agents to ocular tissue. The present disclosure is directed to an ophthalmic device comprising a hydrogel comprising integral PC groups and a releasable ionic agent electrostatically bound to the PC groups. Phosphorylcholine is zwitterionic, containing both a negative charge and a positive charge at relatively close proximity, and thus would be expected to act as a net-neutral molecule. However, we have found that it can be used to attach to and release both anionic and cationic agents. In specific examples, the ionic agent is polyionic and/or comprises at least one guanidinium cation. Contact lenses are exemplified herein, however other types of ophthalmic devices made from hydrogels, such as ocular inserts, ocular bandages, and intraocular lenses can be made in accordance with the present disclosure. The ophthalmic device is provided unworn (i.e. it is a new device, not having been previously used by a patient) sealed in a package, such as a blister package, glass vial, or other suitable package, containing a packaging solution in which the ophthalmic device is immersed.

The hydrogel can be manufactured by polymerizing a monomer mixture to form a polymerization product, and hydrating the polymerization product to obtain the hydrogel. As used herein, the term "monomer mixture" refers to a mixture of polymerizable monomers together with any additional ingredients, including non-polymerizable ingredients, which are subjected to polymerization conditions to form a polymerization product. In the case of contact lenses, so-called "conventional hydrogels" are typically formed from a monomer mixture comprising a hydrophilic monomer such as 2-hydroxyethyl methacrylate (HEMA) or vinyl alcohol, together with a cross-linking agent, optionally in combination with other monomers, and containing no siloxane (i.e. a molecule comprising at least one Si—O group). A silicone hydrogel is formed from a monomer mixture that comprises at least one polymerizable siloxane monomer. The term "monomer" refers to any molecule capable of reacting in a polymerization reaction with other molecules that are the same or different, to form a polymer or copolymer. Thus, the term encompasses polymerizable pre-polymers and macromers, there being no size-constraint of the monomer unless indicated otherwise.

The hydrogel ophthalmic device comprises integral PC groups, meaning that the PC groups are covalently attached to the polymer matrix of the hydrogel. The hydrogel may include additional integral ionic components that may electrostatically bind to the ionic agent provided that a significant amount of the ionic agent binds to the PC groups as determined using an in vitro uptake assay as described below. In some examples, the phosphorylcholine groups provide the only integral ionic groups of the hydrogel. In one example the monomer mixture used to make the hydrogel comprises a polymerizable monomer having a PC group. An exemplary monomer is 2-methacryloyloxyethyl phosphorylcholine (MPC). In a specific example, the monomer mixture comprises at least 5, 10, or 15%, and up to about 20, 30, or 40% MPC, where percentages are weight percentages based on the total weight of all polymerizable components in the monomer mixture (i.e. excluding non-polymerizable components such as diluents, etc.). Omalfilcon A contact lenses, sold under the brand name Proclear, are made from polymerization of a monomer mixture comprising about 83 wt. % HEMA, about 16 wt. % MPC, about 1 wt. % ethyleneglycol dimethacrylate (EGDMA), and a tinting agent. Silicone monomers comprising PC groups can also be used to prepare silicone hydrogels (see e.g. US Pat. Publ. No. 2012/0136087). Alternatively, or in addition to including a PC-containing monomer in the monomer mixture a hydrogel comprising integral PC groups may be prepared by attaching PC to an already cured polymerization product or hydrogel (see e.g. U.S. Pat. No. 5,422, 402). The amount of integral PC groups incorporated into the hydrogel can be adjusted to provide desirable uptake and release properties for a selected ionic agent. In some examples, the hydrogel comprises at least 2, 5, 10, or 15 wt. % and up to about 20, 25, 30, or 35 wt. % of PC groups, where wt. % is based on the total weight of the integral components of the non-hydrated hydrogel, and 182 is taken as the molecular weight for each PC group (i.e. each —$PO_4C_2H_4N(CH_3)_3$).

All percentages provided herein are percentage by weight unless indicated otherwise. Throughout this disclosure, when a series of lower limit ranges and a series of upper limit ranges are provided, all combinations of the provided ranges are contemplated as if each combination were specifically listed. For example, in the listing of PC group weight percentages provided in the preceding paragraph, all 16 possible ranges of weight percentages are contemplated (i.e. 2-20 wt. %, 5-20 wt. % ... 15-30 wt. %, and 15-35 wt. %). Further, throughout this disclosure when a series of values is presented with a unit of measurement following the last value of the series, the unit of measurement is intended to implicitly follow each preceding value in the series unless context indicates otherwise. For example, in the previous listing of PC group weight percent ranges, it is intended that the unit of measurement "wt. %" implicitly follows the values of 2, 5, 10, 20, 25, and 30. Also, throughout this disclosure, when a series of values is presented with a qualifier preceding the first value, the qualifier is intended to implicitly precede each value in the series unless context dictates otherwise. For example, for the values of the previous listing of PC group weight percentages, it is intended that the qualifier "at least" implicitly precedes 5, 10 and 15, and the qualifier "to about" implicitly precedes 25, 30 and 35. Additionally, throughout this disclosure a reference to "examples", "one example", "a specific example" or similar phrase, is intended to introduce a feature or features of the contact lens, monomer mixture, ionic agent, packaging solution, method of manufacture, etc. (depending on context) that can be combined with any combination of previously-described or subsequently-described examples (i.e. features), unless a particular combination of features is mutually exclusive, or if context indicates otherwise.

The remaining components of the monomer mixture, the method of polymerizing the monomer mixture to make a polymerization product, and the method of hydrating the polymerization product to make a hydrogel can be conventional. Exemplary monomer mixture components and polymerization methods are described in U.S. Pat. No. 6,867,245, to Iwata et al., U.S. Pat. No. 8,129,442 to Ueyama et al., U.S. Pat. No. 4,889,664 to Kindt-Larsen et al., U.S. Pat. No. 3,630, 200 to Higuchi, and U.S. Pat. No. 6,217,896 to Benjamin, and WO 2012/118680 to Liu et al, each incorporated herein by reference. In the case of contact lenses, the monomer mixture is filled into a contact lens mold, which is typically made from a thermoplastic polymer such as polypropylene. Typically, a first mold member defining the front surface of the contact lens, referred to as a "female mold member", is filled with an amount of the monomer mixture sufficient to form a single lens-shaped polymerization product. A second mold member defining the back (i.e. eye-contacting) surface of the contact lens, referred to as the "male mold member", is coupled to the female mold member to form a mold assembly having a lens-shaped cavity with the amount of monomer mixture in between the two mold members. The monomer mixture within the contact lens mold assembly is then polymerized using any suitable curing method. Typically, the monomer mixture is exposed to polymerizing amounts of heat or ultraviolet light (UV). In the case of UV-curing, also referred to as photopolymerization, the monomer mixture typically comprises a photoinitiator such as benzoin methyl ether, 1-hydroxycyclohexylphenyl ketone, Darocur or Irgacur (available from Ciba Specialty Chemicals). Photopolymerization methods for contact lenses are described in U.S. Pat. No. 5,760, 100. In the case of heat-curing, also referred to as thermal curing, the monomer mixture typically comprises a thermal initiator. Exemplary thermal initiators include 2,2'-azobis(2, 4-dimethylpentanenitrile) (V-52), 2,2'-Azobis(2-methylpropanenitrile) (V-64), and 1,1'-azo bis(cyanocyclohexane) (V-88).

After cure, the mold is opened and the resulting lens-shaped polymerization product is either mechanically removed from the mold (i.e. dry-delensed) or is wet-delensed by immersing the mold in a liquid until the polymeric lens body hydrates and floats off of the mold. After delensing, the polymeric lens body may be washed to hydrate the lens and/or remove extractable components from the lens, or the lens may be placed directly into its final package containing a packaging solution without a post-delensing washing step. Thus, in one example, the lens is dry when placed into its final package. In another example, the lens may be partially or fully hydrated when placed in its final package. The package is then sealed and optionally sterilized. Suitable sterilization methods include autoclaving, gamma radiation, e-beam radiation, ultraviolet radiation, etc. In some examples, the hydrogel and packaging solution may be manufactured and combined using sterile conditions making a post-packaging sterilization step unnecessary.

The package may be a hermetically sealed blister-pack, in which a concave well containing a contact lens is covered by a metal or plastic sheet adapted for peeling in order to open the blister-pack. The package may be any other suitable inert packaging material providing a reasonable degree of protection to the lens, such as a glass vial or a package made from a plastic such as polyalkylene (e.g., polyethylene or polypropylene), PVC, polyamide, and the like. Generally, the final manufactured product includes at least a sealed package containing an unused contact lens immersed in an aqueous packaging solution as further exemplified herein.

Typically, the ionic agent will be bound to the hydrogel simply by preparing a packaging solution comprising the ionic agent and immersing a hydrogel or polymerization product comprising integral PC groups into the packaging solution. The PC groups of the hydrogel attract and electrostatically bind to the ionic agent. Alternatively, or additionally, the ionic agent can be incorporated into a hydrogel by adding the agent into the monomer mixture used to form the polymerization product. The polymerization product is then packaged with a packaging solution either containing no ionic agent or containing additional ionic agent.

An ionic agent is considered to electrostatically bind to the PC groups of the hydrogel if the hydrogel takes up a significantly higher amount of the ionic agent compared to a hydrogel of substantially the same size and dimensions lacking the PC groups, but otherwise comprising the same components, as measured using an uptake assay substantially as described in Example 1 below. For example, polymacon 38 contact lenses, sold under the brand name Biomedics 38, are made from the polymerization of HEMA and EGDMA and comprise the same tinting agent as Proclear 1-Day lenses, and thus are comparable lenses for assessing electrostatic binding of an ionic agent to Proclear lenses. In some examples, a hydrogel comprising integral PC groups takes up at least 20, 50, 100, or 200 wt. % more of the ionic agent than a comparative lens lacking the PC groups. Typically, in the case of contact lenses, the amount of ionic agent bound is at least 10, 20, 25, 50, 75, or 100 µg/lens and up to about 150, 200, 250, 300 µg/lens or more. The ionic agent is considered "releasable" if at least 10% of the agent releases from the hydrogel within 24 hours when tested in an in vitro release assay substantially as described in Example 1 below. In various examples, at least 20, 40, 60 or 80% of the agent releases from the hydrogel by 24 hours.

We have found that hydrogels comprising integral PC groups have unique uptake and release properties of agents comprising one or more cationic guanidinium groups. As used herein, the term "guanidinium group" refers to a positively charged group comprising a central carbon atom covalently bonded to three nitrogen atoms, with a double bond between one of the nitrogen atoms and the central carbon. Exemplary beneficial agents for ophthalmic applications that comprise at least one guanidinium group include antihistamines such as epinastine and emedastine; glaucoma drugs such as apraclonidine and brimonidine; guanine derivative antiviral agents such as ganciclovir and valganciclovir; arginine-containing antimicrobial peptides such as the defensins and indolicidin; and biguanide-based antimicrobial agents such as chlorhexidine, alexidine, and polyhexamethylene biguanide (PHMB). References herein to a specific ionic agent are intended to encompass the agent and any of its ophthalmically-acceptable salts. For example, as used herein, the term "epinastine" refers to epinastine as well as epinastine hydrochloride. In various examples, the ionic agent comprises at least 1, 2, 4, and up to about 10, 15, 20, or more guanidinium groups. In other examples, the ionic agent comprises at least 1, 2, 4, and up to about 10, 15, 20, 50 or more biguanide groups. In yet another example the ionic agent comprises or consists of at least 1, 2, 4, and up to about 10, 15, 20, or more arginine groups. In such example, the ionic agent may be a naturally-occurring peptide or synthetic peptide, particularly an antimicrobial peptide. In a specific example, the peptide is polyarginine.

In another example, the ionic agent is a polymer. The polymer may be anionic, cationic, or zwitterionic provided that it electrostatically binds the PC groups of the hydrogel and is releasable. In some examples the polymer is cationic and comprises at least 4, 6, 8, 10, 15, 20 or more cationic groups. In other examples, the polymer is anionic and comprises at least 4, 6, 8, 10, 15, 20 or more anionic groups. Exemplary cationic polymers include epsilon polylysine (ePLL), antimicrobial peptides which comprise multiple arginine and/or lysine groups, PHMB, and quaternary ammonium compounds (i.e. polyquats). Exemplary anionic polymers include sulfonate-group containing polymers such as polystyrene sulfonate and anionic polysaccharides such as alginate, xanthan gum, gellan gum, and hyaluronic acid. We have found that polystyrene sulfonate (PSS) can significantly decrease the coefficient of friction of Proclear lenses. Thus in one example the agent is polystyrene sulfonate. In specific examples, the agent is a polystyrene sulfonate having an average molecular weight of from about 50K, 75K, 100K or 500K up to about 1M, 2M, or 4M. In further examples, the PSS is provided in a packaging solution at a concentration of about 50, 250, or 500 ppm up to about 1000, 2500 or 5000 ppm. We have also found that polyquaternium-55, sold under the tradename Styleze® W-20, significantly decreases the coefficient of friction of omalfilcon A contact lenses even after washing the lenses overnight in PBS. Thus, in a specific example, the ionic agent is polyquaternium-55 and is included in the packaging solution at a concentration of about 0.01, 0.05, or 0.1% up to about 0.5%, 1.0%, or 2.0%.

We have shown that hydrogels comprising integral PC groups can sustain release of certain ionic agents for 12 hours or more. This may be beneficial for therapeutic applications where continuous drug delivery is advantageous over delivery by ophthalmic drops. As used herein, a hydrogel comprising integral PC groups is said to exhibit "sustained release" of an ionic agent for at least a given duration of time if there is a significant increase in cumulative amount of the ionic agent released between the end of that given duration of time and the next time duration of time tested as determined in an in vitro release assay substantially as described in Example 1. For example, if a hydrogel releases 30 µg of an ionic agent between 0-2 hours, and releases an additional 30 µg of the ionic agent between 2-6 hours, as determined using the in vitro release assay, the hydrogel is said to sustain release of the ionic agent for at least 2 hours. In some examples, the hydrogel sustains release of the ionic agent for at least 6 hours or 24 hours. The amount of PC in the lens and the concentration of the ionic agent in the packaging solution (and/or in the monomer mixture) can be balanced to provide desirable release profiles.

Example 1 demonstrates the unique release properties of a hydrogel contact lens comprising integral PC groups, Proclear, compared to a nonionic silicone hydrogel lens, an ionic silicone hydrogel lens, and a conventional ionic hydrogel lens comprising HEMA and about 1.8 wt. % methacrylic acid. This example evaluated the release of PHMB, a polycationic polymer used to treat Ancanthamoeba infections, a condition which can lead to blindness if left untreated. The nonionic silicone hydrogel lens took up less than 10% the amount of PHMB that was taken up by the Proclear lens and released about 50% of its PHMB within the first two hours of the release assay; it exhibited no significant PHMB release beyond the two hour time point. In contrast, the PC-containing lenses sustained PHMB release for at least 24 hours. Although the conventional ionic hydrogel lens took up about 30% more PHMB than the Proclear lens, it evidently bound to PHMB much more strongly, as it released only about 40% or less of the amount released by the Proclear lenses at each of the time points tested. Unlike anionic lenses, hydrogels comprising integral PC-groups can also sustain release of an anionic polymer, as demonstrated with polystyrene sulfonate in Example 8 below. Thus, in various examples, the hydrogel comprising integral phosphorylcholine groups sustains release of an ionic agent for at least 2, 6, or 24 hours, as determined using a release assay substantially as described in Example 1. In some examples, the ionic agent is a cationic polymer. In other examples, the ionic agent is an anionic polymer.

We have found that by decreasing the ionic strength of the packaging solution from what is conventionally used for ophthalmic devices, such as contact lenses, uptake of an ionic agent by a hydrogel comprising integral PC groups can be significantly increased. For example, hydrated Proclear contact lenses were packaged and autoclaved in PBS having an ionic strength of about 0.2 and comprising 500 ppm ePLL, an antimicrobial peptide. These lenses took up an average of 5 µg of the ePLL/lens. The lenses were found to have no antimicrobial activity against the ocular pathogen, *Serratia marcescens*. In contrast, the same Proclear lenses packaged and autoclaved in TRIS buffer with 2% sorbitol, which has an ionic strength of about 0.02, took up an average of about 120 µg ePLL/lens and resulted in about a 4-log kill of *Serratia marcescens*. Thus, in various examples, the packaging solution has an ionic strength of less than about 0.15, 0.10, or 0.05 as calculated by the equation:

$$I = \frac{1}{2}\sum_{i=1}^{n} c_i z_i^2$$

where $c_i$ is the molar concentration of ion i (mol·dm$^{-3}$), $z_i$ is the charge number of that ion and the sum is taken over all ions in the solution. To reduce ionic strength while maintaining proper osmolality in the range of about 200 mOsm/kg to about 400 mOsm/kg, sodium chloride, which is commonly used as a tonicity agent in contact lens packaging solutions, can be replaced with a non-electrolyte tonicity agent, such as sorbitol, as indicated above. Other non-electrolyte tonicity agents that can be used in the packaging solution include mannitol, sucrose, glycerol, propylene glycol, xylitol, inositol, polyethylene glycols, polypropylene glycols, and mixtures thereof. In some examples, the osmolality of the packaging solution is at least about 250 or 270 mOsm/kg up to about 310, or 350 mOsm/kg. In some examples, the packaging solution consists, or consists essentially, of an aqueous solution of a buffer, a tonicity agent, and the ionic agent. In other examples, the packaging solution contains additional agents such as an antimicrobial agent, a comfort agent, a hydrophilic polymer, or a surfactant or other additive that prevents the lens from sticking to the package. The packaging solution typically has a pH in the range of about 6.8 or 7.0 up to about 7.8 or 8.0.

Hydrogel contact lenses comprising integral PC groups can uptake and release ionic agents without significantly altering the dimensions of the lens (e.g. lens diameter and base curve), lens clarity (i.e. the lenses are optically clear, having at least 93%, 95%, or 97% light transmittance between 380 nm to 780 nm as measured in accordance with ISO 18369), or physical properties such as Young's Modulus or tensile strength.

In various examples the contact lens is an extended-wear contact lens which a patient wears continuously for at least 24 hours, 5 days, 7 days, or 14 days. In another example the contact lens is a daily-disposable lens which is worn by a patient during waking hours, removed and discarded prior to sleep, and replaced by a new, unworn lens each day. In a further example, the contact lens is a daily-wear lens which a patient wears during the day and stores each night in a solution intended for contact lens storage. In such example, the contact lens storage solution may comprise an additional dose of the ionic agent which incorporates into the contact lens and electrostatically binds to the PC groups during the overnight storage, thereby replenishing ionic agent that was released from the previous daytime wear of the lens.

We have found that uptake of certain ionic agents is significantly higher if the polymerization product is non-hydrated when immersed into a packaging solution comprising the anionic agent. The higher uptake remains even after autoclaving the packaged hydrogel. Thus, in a specific example, the method comprises polymerizing a monomer mixture comprising MPC in a contact lens mold to provide a non-hydrated lens-shaped polymerization product, removing the polymerization product from the mold, immersing the non-hydrated lens-shaped polymerization product in a package containing a packaging solution comprising an ionic agent, and sealing the package, wherein the ionic agent electrostatically attaches to phosphorylcholine groups on the MPC. In various examples the ionic agent is polyionic or comprises at least one guanidinium group or is both polyionic and comprises at least one guanidinium group. Any of the previously-described specific ionic agents, classes of ionic agents, and amounts thereof may be included in the packating solution. The method may comprise the further step of autoclaving the sealed package.

The ophthalmic devices described herein can be used in a method of administering a beneficial agent to a patient in need of the agent. The method comprises providing the patient with a hydrogel comprising integral phosphorylcholine groups and a releasable ionic agent electrostatically bound to the phosphorylcholine groups. The ionic agent is polyionic or comprises at least one guanidinium group or is both polyionic and comprises at least one guanidinium group. In various examples, the beneficial agent delivered by the ophthalmic device is indicated for the prevention or treatment of an ophthalmic disease, disorder, or infection with which the patient has been diagnosed or of which the patient has been determined to be at risk. For example, the agent may be an antihistamine such as epinastine or emedastine for the treatment of allergic conjunctivitis. In another example the agent is a glaucoma drug such as apraclonidine or brimonidine. In a further example the agent is a guanine derivative antiviral agent such as ganciclovir or valganciclovir for the treatment of herpetic keratitis or other viral infection. In yet another example, the agent is an antimicrobial agent indicated for the treatment of microbial keratitis, such as a defensin, indolicidin, ε-PLL, chlorhexidine, or PHMB. In still a further example, the agent is a comfort polymer used for the treatment of symptoms of dry eye disease or contact lens intolerance. In various examples the ophthalmic device is selected from a contact lens, an ocular insert, an ocular bandage, and an intraocular lens.

The following Examples illustrate certain aspects and advantages of the present invention, which should be understood not to be limited thereby.

EXAMPLE 1

Uptake and Release of PHMB by MPC-Containing Contact Lenses

The uptake and release of PHMB from commercially-available Proclear 1-Day (omalfilcon A) contact lenses was compared with a commercially-available, non-ionic silicone hydrogel lens (Biofinity), a commercially-available, ionic HEMA lens comprising about 1.8 wt. % methacrylic acid (Biomedics 55), and an ionic silicon hydrogel lens comprising about 1.8 wt. % methacrylic acid (SiHy-MA). Proclear lenses are prepared from a monomer mixture comprising about 83 wt. % 2-hydroxyethylmethacrylate (HEMA), about 16 wt. % 2-methacryloyloxyethyl phosphorylcholine (MPC), and about 1% cross-linking agent, where wt. % is based on the total weight of polymerizable monomers in the monomer mixture.

Ionic Agent Uptake Assay:

The lenses were removed from their packaging, vortexed in deionized water three times, then allowed to equilibrate overnight in deionized water at room temperature. The lenses were then placed in 6 ml glass vials containing 1.2 ml of 500 ppm PHMB in PBS. Unless indicated otherwise, references herein to PBS mean an aqueous solution of 0.83 wt. % NaCl, 0.03 wt. % sodium phosphate monobasic, and 0.24% sodium phosphate dibasic having a pH of 7.3. The samples in vials were kept on a shaker and maintained at 25° C. for the duration of the uptake. At 2, 6, and 24 hours, and once a day thereafter until uptake was complete, the packing solution was tested by HPLC for PHMB concentration. Uptake was considered complete when the PHMB concentration of the packing solution stopped decreasing. After uptake was complete, the lenses were tested for PHMB release as described below. Controls of PHMB solution without lenses were also tested.

Ionic Agent Release Assay:

Cumulative release of PHMB from the lenses was tested by transferring each lens to 1.0 ml ISO 10344 release media in 6 ml lens vials. Samples in vials were kept in a heated shaker at 37° C. for the duration of release. At 2, 6, and 24 hours, and once a day thereafter, the packing solution was tested by HPLC for amount of PHMB released and the lenses were transferred to fresh vials of ISO10344 for continued PHMB release. Tables 1 and 2 summarize the uptake and release data, respectively.

TABLE 1

| | PHMB uptake (μg) | | | | | |
|---|---|---|---|---|---|---|
| Lens | 2 hr | 6 hr | 24 hr | 48 hr | 72 hr | 96 hr |
| Biofinity | 36 | 44 | 40 | 39 | 41 | 29 |
| Proclear | 292 | 383 | 372 | 419 | 418 | 420 |
| Biomedics 55 | 366 | 523 | 543 | 589 | 589 | 589 |
| SiHyMA | 224 | 358 | 418 | 493 | 495 | 494 |

TABLE 2

| | cumulative PHMB release (μg (%)) | | | | |
|---|---|---|---|---|---|
| Lens | 2 hr | 6 hr | 24 hr | 48 hr | 96 hr |
| Biofinity | 17 (39) | 17 (39) | 17 (39) | 17 (39) | 17 (39) |
| Proclear | 35 (9) | 68 (18) | 85 (22) | 99 (26) | 99 (26) |
| Biomedics 55 | 12 (2) | 24 (5) | 33 (6) | 41 (8) | 41 (8) |
| SiHy-MA | 16 (5) | 26 (7) | 32 (9) | 36 (10) | 36 (10) |

By comparison, the same experiment was carried out except that the lenses were packaged with 500 ppm PQ1 in PBS. The Proclear lenses took up an average of 11 μg PQ1, whereas the Biomedics 55 lenses took up an average 282 μg PQ1.

EXAMPLE 2

Uptake of Epinastine by MPC-Containing Contact Lenses

Uptake of epinastine from Proclear contact lenses was compared to uptake by a non-ionic silicone hydrogel lens (Biofinity) using substantially the same methods as described in Example 1, except that the uptake solution consisted of 50 ppm epinastine solution in TRIS buffer with 3% sorbitol (0.02% TRIS (hydroxymethyl) amino methane, 0.26% trizma hydrochloride, 2.85% sorbitol, and 94.97% deionized $H_2O$; "Tris-Sorbitol). The Proclear lenses took up an average of about 38 μg epinastine, whereas the Biofinity lenses took up an average of about 14 μg epinastine.

EXAMPLE 3

Uptake of Cromolyn: Dry vs Wet Loading

The ability of hydrated and non-hydrated (dry) Proclear lenses to take up olopatadine, ketotifen, and cromolyn was evaluated. At physiological pH, olopatadine is zwitterionic, ketotifen is positively charged, and cromolyn is negatively charged. Each drug was prepared at low and high concentrations: 25 μg/ml and 250 μg/ml ketotifen in borate buffer (pH 7.51), 200 μg/ml and 1000 μg/ml olopatadine in PBS, and 400 μg/ml and 2000 μg/ml cromolyn in PBS. The hydrated Proclear lenses were removed from their packages and washed with PBS as described in Example 1, packaged in 3 ml of each drug solution, and autoclaved. The dry lenses were removed from their original molds, packaged with 3 ml of each drug solution without any intermediate hydration step and autoclaved. For controls, each drug solution was packaged without a lens and autoclaved. After autoclave, the amount of drug in each packaging solution was measured by HPLC. Table 3 shows the average drug uptake by each lens (n=3), which was calculated as the difference between the control packaging solution and the lens packaging solution. The % increase or decrease in drug loading by dry lenses compared to wet lenses is shown. The dry lenses took up significantly more of the negatively charged drug, cromolyn, at both the low and high concentrations of the drug.

TABLE 3

| | Drug Uptake (μg) | | |
|---|---|---|---|
| Drug | Dry Lens | Wet Lens | % Δ Dry vs Wet |
| 25 μg/ml ketotifen | 10 | 12 | −17% |
| 250 μg/ml ketotifen | 115 | 122 | −6% |
| 200 μg/ml olopatadine | 52 | 45 | 16% |
| 1000 μg/ml olopatadine | 215 | 202 | 6% |
| 400 μg/ml cromolyn | 47 | 32 | 47% |
| 2000 μg/ml cromolyn | 155 | 81 | 91% |

EXAMPLE 4

Uptake of ePLL in Low Ionic Strength Packaging Solution

The uptake and release of ePLL from non-hydrated (i.e. dry) Proclear lenses was evaluated. The ePLL (Chisso Corporation, Tokyo, Japan) was prepared at a concentration of 500 ppm in three different buffers, PBS, TRIS buffered saline (0.023% tris(hydroxymethyl)methylamine, 0.544% trizma hydrochloride, 0.819% NaCl; TBS), or Tris-sorbitol. Lenses were individually packaged, in triplicate, in 1.2 ml of each ePLL preparation and autoclaved. Additionally, vials containing 1.2 ml 500 ppm ePLL in each buffer with no lens (control vials) were also autoclaved. The amounts of ePLL present in the post-autoclave solution of the test lens vials and in the control vial were determined by cationic size exclusion chromatography using a sample injection volume of 5 μl, a Water Acquity UPLC BEH 125 SEC 1.7 μm 4.6×150 mm at room temperature, and a flow rate of 0.4 ml/min using 90% 0.2M NaCl/0.1% TFA in $H_2O$: 10% ACN isocratically. The average of the amount of ePLL taken up by each test lens (n=3) was calculated by subtracting the amount of ePLL present in the post-autoclave solution of the test lens vial from the amount of ePLL present in the control vial. Lenses packaged with 500 ppm ePLL in PBS took up an average of 88 μg ePLL. Lenses packaged with 500 ppm ePLL in TBS took up 47 μg ePLL, and lenses packaged with 500 ppm ePLL in Tris-sorbitol took up 208 μg ePLL.

EXAMPLE 5

Uptake of Anionic Polymer by Hydrated and Non-Hydrated Proclear Lenses

Hydrated and non-hydrated Proclear lenses were individually placed in 6 ml glass vials containing 3 ml of 0.01 mole/ liter of polystyrene sulfonate (PSS) having a molecular weight of 145K, 3K or 206 (monomer). After 48 hours the PSS concentration in each vial was measured by UV spectroscopy at 273.5 nm. The average for each condition (n=3) is shown in Table 4. The dry lens took up significantly more styrene sulfonate monomer (Mol. Wt. 206) than the wet lens.

TABLE 4

| PSS Mol. Wt. | Uptake (µg) | | |
|---|---|---|---|
| | Dry Lens | Wet Lens | % Δ Dry vs Wet |
| 145K | 301 | 308 | −2% |
| 3K | 128 | 127 | 1% |
| 206 | 110 | 92 | 16% |

EXAMPLE 6

Uptake and Release of Anionic Polymer by Proclear Lenses

Three non-hydrated Proclear lenses were individually placed in 6 ml glass vials containing 3 ml of 1000 µg/ml of 77K molecular weight polystyrene sulfonate (PSS) in PBS, sealed, and autoclaved. A control vial containing 3 ml of the PSS solution was also autoclaved. The concentration in each vial was measured by UV spectroscopy at 273.5 nm and the amount of PSS taken up by each lens was calculated as the difference in PSS concentration between the control and test vials. The lenses took up an average of 246 µg of the PSS. The lenses were tested for release of PSS using the release assay substantially as described in Example 1, except that on day 1 the time points tested were 1 hr, 3 hr, 5 hr, and 7 hr. The average cumulative release in µg and % is shown in Table 5.

TABLE 5

| Cumulative release of 77 K PSS | | | | | | | | | |
|---|---|---|---|---|---|---|---|---|---|
| 1 hr | 3 hr | 5 hr | 7 hr | 24 hr | 48 hr | 72 hr | 96 hr | 168 hr | 240 hr |
| 12 µg | 28 µg | 41 µg | 50 µg | 54 µg | 58 µg | 58 µg | 60 µg | 64 µg | 69 µg |
| 5% | 11% | 17% | 20% | 22% | 24% | 24% | 25% | 26% | 28% |

Although the disclosure herein refers to certain illustrated examples, it is to be understood that these examples are presented by way of example and not by way of limitation. The intent of the foregoing detailed description, although discussing exemplary examples, is to be construed to cover all modifications, alternatives, and equivalents of the examples as may fall within the spirit and scope of the invention as defined by the additional disclosure.

A number of publications and patents have been cited hereinabove. Each of the cited publications and patents are hereby incorporated by reference in their entireties.

The invention further provides:

1. A sealed package containing a contact lens immersed in a packaging solution, said contact lens comprising a hydrogel comprising phosphorylcholine groups; and an ionic agent that is polyionic or comprises at least one guanidinium group or is both polyionic and comprises at least one guanidinium group. Advantageously, the ionic agent is electrostatically bound to the phosphorylcholine groups of the hydrogel and releases the ionic agent upon being worn by a patient.

2. The package of 1, wherein the hydrogel comprises a hydrated polymerization product of a monomer mixture comprising 2-methacryloyloxyethyl phosphorylcholine (MPC).

3. The package of 2, wherein the monomer mixture comprises about 10 wt. % to 20 wt. % MPC.

4. The package of any one of 1-3, wherein the ionic agent comprises at least one guanidinium group.

5. The package of any one of 1-3, wherein the ionic agent is selected from epinastine, PHMB, polyarginine, epsilon polylysine, polystyrene sulfonate, and polyquaternium-55.

6. The package of any one of 1-4, wherein the ionic agent is polyionic.

7. The package of any one of 1-3, wherein the ionic agent comprises at least two arginine groups.

8. The package of any one of 1-3, wherein the ionic agent comprises at least two sulfonate groups.

9. A method of manufacturing a contact lens, said method comprising:
 a) polymerizing a monomer mixture comprising 2-methacryloyloxyethyl phosphorylcholine (MPC) to provide an non-hydrated lens-shaped polymerization product;
 b) immersing the non-hydrated lens-shaped polymerization product in a package containing a packaging solution comprising an ionic agent; and
 c) sealing the package. The ionic agent advantageously electrostatically attaches to the phosphorylcholine groups on the MPC.

10. The method of 9, wherein the monomer mixture comprises 10 wt. % to 20 wt. % MPC.

11. The method of 9 or 10, wherein the ionic agent is polyionic or comprises at least one guanidinium group or is both polyionic and comprises at least one guanidinium group.

12. The method of 9 or 10, wherein the ionic agent is cationic.

13. The method of 9 or 10, wherein the ionic agent is anionic.

14. The method of 9 or 10, wherein the ionic agent is polyquaternium-55.

15. The method of 9 or 10, further comprising autoclaving the sealed package.

16. The package of any one of 1 to 8 above, or the contact lens manufactured by the method of any one of 9 to 15 above, for administering an ionic agent to ocular tissue of a patient in need thereof.

We claim:

1. An unworn contact lens immersed in a packaging solution and sealed in a package, said contact lens comprising:
 (a) a hydrogel comprising integral phosphorylcholine groups; and
 (b) a releasable ionic agent electrostatically bound to the phosphorylcholine groups, wherein the ionic agent is polyionic or comprises at least one guanidinium group or is both polyionic and comprises at least one guanidinium group.

2. The contact lens of claim 1, wherein the hydrogel comprises a hydrated polymerization product of a monomer mixture comprising 2-methacryloyloxyethyl phosphorylcholine (MPC).

3. The contact lens of claim 2, wherein the monomer mixture comprises about 10 wt. % to 20 wt. % MPC.

4. The contact lens of claim 1, wherein the ionic agent is epinastine.

5. The contact lens of claim 1, wherein the ionic agent is polyionic.

6. The contact lens of claim 1, wherein the ionic agent comprises at least one guanidinium group.

7. The contact lens of claim 1, wherein the ionic agent comprises at least two guanidinium groups.

8. The contact lens of claim 1, wherein the ionic agent is polyhexamethylene biguanide.

9. The contact lens of claim 1, wherein the ionic agent comprises at least two arginine groups.

10. The contact lens of claim 1, wherein the ionic agent is polyarginine.

11. The contact lens of claim 1, wherein the ionic agent is epsilon polylysine.

12. The contact lens of claim 1, wherein the ionic agent comprises at least two sulfonate groups.

13. The contact lens of claim 1, wherein the ionic agent is polystyrene sulfonate.

14. The contact lens of claim 1, wherein the agent is 1-Dodecanaminium N,N-dimethyl-N-(3-((2-methyl-1-oxo-2-propenyl)amino)propyl)-chloride, polymer with N-(3-(dimethylamino)propyl)-2-methyl-2-propenamide and 1-ethenyl-2-pyrrolidone (polyquaternium-55).

\* \* \* \* \*